(12) United States Patent
Gerhardt et al.

(10) Patent No.: US 8,236,130 B2
(45) Date of Patent: Aug. 7, 2012

(54) SEALING LIQUID

(75) Inventors: Thomas Gerhardt, Berlin (DE); Wolfgang Muhl, Hohen Neuendorf (DE)

(73) Assignee: Francotyp-Postalia GmbH, Birkenwerder (DE)

( * ) Notice: Subject to any disclaimer, the term of this patent is extended or adjusted under 35 U.S.C. 154(b) by 37 days.

(21) Appl. No.: 12/966,086

(22) Filed: Dec. 13, 2010

(65) Prior Publication Data

US 2011/0139337 A1    Jun. 16, 2011

Related U.S. Application Data

(62) Division of application No. 11/690,243, filed on Mar. 23, 2007, now Pat. No. 7,892,393.

(30) Foreign Application Priority Data

Mar. 24, 2006   (DE) .................. 10 2006 014 164

(51) Int. Cl.
*B65B 7/00* (2006.01)
*B44C 1/165* (2006.01)
*C04B 37/00* (2006.01)
*B43M 3/00* (2006.01)
*B32B 7/12* (2006.01)
*B32B 15/04* (2006.01)

(52) U.S. Cl. ........ 156/325; 156/69; 156/230; 156/442.2; 428/343

(58) Field of Classification Search ............... 156/69, 156/230, 325, 442.2; 428/343
See application file for complete search history.

(56) References Cited

U.S. PATENT DOCUMENTS

| 5,674,304 A | 10/1997 | Auslander et al. |
| 6,551,391 B1 | 4/2003 | Gerhardt et al. |
| 7,384,500 B2 | 6/2008 | Lüdke |

*Primary Examiner* — Michael Orlando
(74) *Attorney, Agent, or Firm* — Schiff Hardin LLP

(57) ABSTRACT

The invention concerns a sealing liquid comprising water and a penetration agent for sealing of mail pieces, the use of said sealing liquid as well as sealing devices and franking machines containing such a sealing liquid.

8 Claims, No Drawings

SEALING LIQUID

RELATED APPLICATION

The present application is a divisional application of Ser. No. 11/690,243, filed on Mar. 23, 2007, now U.S. Pat. No. 7,892,393, the contents of which are incorporated herein by reference.

FIELD OF THE INVENTION

The invention relates to a sealing liquid comprising water, in particular for sealing mail pieces, and to the uses of such a sealing liquid as well as to letter sealing devices and franking machines containing such a sealing liquid.

Mail pieces (in particular letters) to be sent in large quantities are for the most part automatically sealed and franked by the sender. Among other things, sealing devices and franking machines are used for this, wherein both components are often connected with each other and sometimes form structural units. As an example, reference is made to the citation DE 20 2004 011 390 U1.

In connection with the sealing of mail pieces whose sealing flaps are provided with a gumming, it is necessary to wet the gumming before the sealing. For this a sealing liquid is (automatically) applied to the gumming. A plurality of technological problems are encountered in these contexts. On the one hand, the sealing liquid must sufficiently wet the gumming. Given an insufficient wetting, the sealing liquid will roll off and ultimately there will be no usable bonding is obtained. On the other hand, the amount of sealing liquid applied to the gumming needs to be measured such that on the one hand the gumming adheres, however on the other hand an undesired washing-out or smudging of excessive sealing liquid on the mail piece envelope after sealing does not occur. The latter is important in particular for the prevention of washing-out or smudging of water-sensitive inscriptions or imprints (such as franking stamp imprints) on the mail piece or the mail pieces situated above or below. This has the consequence that the dosing of the sealing liquid is a critical property in the sealing process.

In addition to this, depending on the system sealing devices start with too much water when a sponge of the sealing device is filled with the sealing liquid upon activation of the sealing device. Only after a start-up number of sealed mail pieces does an equilibrium with regard to the amount of sealing liquid contained in the sponge arise in the further (quasi-)continuous operation. As a result, at the beginning of a series of sealings the dose of the sealing liquid will normally be too high since the equilibrium dosage would in turn be too low given adjustment to an initially appropriate dosing. Particularly with the first mail pieces there therefore exists the significant danger of the excess of sealing liquid, with the consequence of the danger of washing-out water-sensitive imprints such as franking stamp imprints.

Furthermore, it is problematic that in practice mail pieces (in particular letters) whose mail piece envelopes or, respectively, letter envelopes are made from paper materials with varying material properties are fed to a sealing device. Paper materials of a low density can thus be significantly more absorbent than paper materials with high density. For a reliable and reproducible sealing of mail pieces with varying paper materials of the mail piece envelope as well, it would therefore be necessary to dose the amount of sealing liquid according to the requirement of the pertaining paper material. Given a material with high absorbency, a comparatively large quantity of sealing liquid would be necessary, since otherwise the sealing liquid would be absorbed quickly and the bonding would not turn out to be sufficient. Given a material of low absorbency, a comparatively small amount of sealing liquid would be required since otherwise the sealing liquid would not be sufficiently absorbed and a washing-out and running of excessive sealing liquid would threaten, with the disadvantageous effects described in the preceding.

Various sealing liquids are known from experience. These are aqueous solutions that on the one hand can contain biocide and fungicide in order to prevent the development of germ colonies and unpleasant odors. On the other hand, a wetting agent can be added. In practice, rinsing agent as a wetting agent is also added by users, for example.

The sealing liquids known insofar satisfy all the requirements since a dosing suitable for all mail pieces, and in fact from the beginning, cannot be set in practice and, depending on the number and kind of the mail pieces, a plurality of insufficient sealings and/or washing-outs is to be assumed.

Furthermore, in a different technical field (the production and sealing of cartons) gummed package tapes or, respectively, mounting tapes are used by means of which cartons are sealed or, respectively, fixed in the shape of a container. The application of these package tapes or, respectively, mounting tapes also often ensues in an automated manner, such that in principle the problems described in the preceding arise in this field.

TECHNICAL PROBLEM OF THE INVENTION

The invention is therefore based on the technical problem to specify a sealing liquid with which, given a defined dosage setting, all fed mail pieces can be sealed with improved reliability, and in fact right from the beginning.

MAIN FEATURES OF THE INVENTION AND PREFERRED EMBODIMENTS

To solve this technical problem, the invention teaches a sealing liquid for sealing of mail pieces, which sealing liquid contains water and a penetration agent.

A penetration agent is a substance, which leads to an absorption time of the sealing liquid in paper materials that is reduced relative to water, in particular by at least 10%, advantageously by at least 20%, most advantageously at least 50% (relating to the absorption time of pure water). Wetting agents are not penetration agents in the sense of the invention. The absorption time is measured as the time in which a drop of the sealing liquid of a volume of 100 pl±5 pl applied onto the paper material has completely penetrated into the paper. The measurement of the absorption time, also called penetration time, is known from inkjet printing technology, for example, reference for this is made to the citation EP 1072653 A2.

It has been found that, in principle, all penetration agents that are also used for aqueous inks in inkjet printing technology can also be used in the framework of the invention.

With the invention it is achieved that a sealing device must be adjusted once to a basic setting of the dosage, whereby this basic setting can in practice be the largest dose required for a reliable sealing under all operating states coming into consideration (envelope with greatest absorbency given adjusted equilibrium of the filling of the sponge). An overdosing (relative to the amount required for a good bonding) of sealing liquid will then in fact ensue in a plurality of sealings; however this does not lead to the washing-outs described above since the excessive sealing liquid quickly penetrates into the paper or carton material of the mail piece envelope under the action of the penetration agent. As a result, all mail pieces fed to the sealing device are reliably sealed with this base setting without undesired washing-outs arising, and in fact independent of the material of the mail piece envelope or whether a sealing series has just started or has already proceeded.

Suitable penetration agents are, for example, C1-8 alkyl esters of C1-8 monocarbonic, dicarbonic, or tricarbonic acids, whereby the carbonic acid can be OH-substituted, in particular in the a position. The carboxyl groups can be completely or partially esterified. Other preferred penetration agents are C1-8 ethers von C1-8 polyols, whereby at least one OH group of the polyol is not etherified. In particular diols or triols are considered as polyols, whereby in the latter case 1 or 2 OH groups can be etherified. C1-8 alkyl can be linear, branched, saturated or unsaturated. For example, methyl, ethyl, propyl, isopropyl, butyl, isobutyl, tert-butyl, pentyl etc. are considered as C1-8 alkyl. C1-8 carbonic acids can be linear or branched, saturated or unsaturated. Formic acid, acetic acid, propionic acid, butyric acid, valeric acid, caproic acid, isobutyric acid, isovaleric acid, acrylic acid, crotonic acid etc. are considered as C1-8 carbonic acids. For example, glycolic acid, lactic acid, mandelic acid, malic acid, tartaric acid and citric acid are considered hydroxycarbonic acids. For example, 1,2-ethanediol, 1,3-propanediol, 1,2-propanediol, 1,4-butanediol, 1,3-butanediol, 1,2-butanediol, etc. are considered as diols. The polyol can comprise one or more ether groups. An example for such a polyol is 2,2'-oxydiethanol (diethylene glycol). Not exclusively named as suitable concrete compounds are: methyl lactate, ethyl lactate, propyl lactate, isopropyl lactate, malic acid diester, malic acid monoester, tartaric acid diester, tartaric acid monoester, ethylene glycol monomethylether, ethylene glycol monoethylether, ethylene glycol monopropylether, ethylene glycol monobutylether, diethylene glycol monomethylether, diethylene glycol monoethylether, diethylene glycol monopropylether, diethylene glycol monobutylether.

With regard to further suitable penetration agents, reference is made only as an example to the citations EP 1072653 A and the citations cited therein, as well as to the citations DE 69628897 T2, U.S. Pat. No. 5,674,314 A.

A sealing liquid according to the invention advantageously comprises a wetting agent, in particular a surfactant wetting agent. The wetting agent can be selected from the group comprising "non-ionic surfactants, amphoteric surfactants, anionic surfactants, cationic surfactants, ricinoleic amide propyl betaine". They are advantageously biodegradable surfactants. Amphoteric surfactants are advantageous preferably used since surprisingly a particularly good wetting of the gumming is therewith achieved.

Furthermore, a sealing liquid can contain one or more of the following additional and/or auxiliary substances: stabilizers and/or buffers, dyes and/or aromatic substances. Naturally, biocides (for instance Parmetol A6 or cetyltrimethylammonium bromide) and/or fungicides can also be added in a usual manner. Substances with authorization as food additives, such as food colors, citral, hexyl hexonate etc. are advantageously considered as dyes and aromatic substances. Stabilizers and/or buffers stabilize components of the sealing liquid that can be hydrolyzed. For instance, Na lactate is a suitable stabilizer or buffer for lactate esters. In particular all typical normal salts such as Na lactate, NaCl, KCl etc. are considered as stabilizers or, respectively, buffers.

A sealing liquid according to the invention advantageously has the following composition: a) 50 to 99.9% water by weight, b) 0.1 to 50.0% penetration agent by weight, c) 0 to 10.0% wetting agent by weight, d) 0 to 10.0% stabilizers and/or buffers by weight, e) 0 to 5.0% dyes by weight, f) 0 to 1.0% aromatic substances by weight and g) 0 to 10.0% typical auxiliary substances by weight, and the components a) to g) always add up to 100% by weight. It can in particular be set up: a) 70 to 99.0, in particular 80 to 99.0% water by weight, b) 1.0 to 30.0, in particular 1.0 to 20% penetration agent by weight, c) 0 to 3.0, in particular 0.01 to 1.0% wetting agent by weight, d) 0 to 3.0, in particular 0.01 to 2.0% stabilizers and/or buffers by weight, e) 0 to 2.0, in particular 0.00001 to 1.0% dyes by weight, f) 0 to 1.0, in particular 0.00001 to 0.001% aromatic substances by weight and g) 0 to 1.0, in particular 0 to 0.1% biocides and/or fungicides and/or other typical auxiliary substances by weight.

A particularly preferred sealing liquid consists of 0.5 to 10% by weight, in particular 1 to 5% penetration agent by weight, in particular a C1-4 alkyl ester of a C1-C4α-hydroxycarbonic acid, for instance ethyl lactate, 0.1 to 2% by weight, in particular 0.2 to 1% wetting agent by weight, in particular an amphoteric surfactant, 0 to 5% by weight, in particular 0.5 to 2% by weight, stabilizer (for example Na lactate) and 0 to 2% by weight, in particular 0.00001 to 0.1% by weight of further additive or auxiliary substances such as dyes, biocides, fungicides and/or aromatic substances.

The invention furthermore concerns the use of a sealing liquid described in the preceding for sealing of mail pieces, whereby a flap provided with a gumming of a mail piece envelope enclosing the mail piece is moistened with the sealing liquid, and whereby the wetted flap is then folded and pressed against an opposed surface of the mail piece envelope and thus the mail piece is sealed. The mail piece can in particular be a letter and the mail piece envelope can be a letter envelope. It is preferred when the wetting of the gumming and the folding and pressing-down of the flap ensues automatically controlled in a letter closing device. Purely as a precaution, however, it is noted that the advantages according to the invention in principle also arise given a manual application of the sealing liquid.

The invention furthermore concerns the use of a sealing liquid according to the invention for fixing and/or closing a carton package, whereby an adhesive tape provided with a gumming is wetted with the sealing liquid, and whereby the wetted adhesive tape is applied to the carton package. It is understood that the side of the adhesive tape provided with the gumming is pressed down onto the carton.

The invention furthermore concerns a letter closing device with a tank containing a sealing liquid according to the invention, and with a wetting rocker which is set up for discharge of sealing liquid from the tank and transfer of discharged sealing liquid onto the gumming of a mail piece inserted into the letter closing device. A suitable letter closing device is, for example, described in the citation DE 20 2004 011 390 U1. The invention finally concerns a franking device with a letter closing device according to the invention.

In the following the invention is described in more detail using examples merely representing embodiments.

EXAMPLE 1

Measurement of the Closing Time

Various sealing liquids were examined in the experiments described in the following. A franking machine Jetmail from the company Francotyp-Postalia GmbH (DEU V 8.64A) with employed Powersealer was used. For a simple changing of the sealing liquid, the hose feed from the reservoir container of the Powersealer was removed and held in a 10 ml beaker with the sealing liquid to be tested. Given a change of the sealing liquid, a new sponge was always used in addition to rinsing of the hoses (service mode) and of the sponge receptacle.

The time needed by the letter envelope from the closer to the Powersealer is approximately 1.5 s. The point in time for the glue test (conditional upon the handling) is approximately 0.5 s from the Powersealer. The total time from wetting is thus at least 2 s. At the Powersealer the wetted flap is pressed down against the envelope only for a fraction of a second. The time after which the envelope flap could no longer be detached without destruction was determined from the wetting of the flap.

EXAMPLE 2

Measurement of the Absorption Time

The absorption time or, respectively, penetration time of the tested sealing liquids occurred in that a 0.5 μl drop, dosed from a disposable capillary pipette (DESAGA GmbH, Germany, Article No. 120192), was placed on a letter envelope. Depending on the surface tension and/or wetting, the drop typically had a diameter of 1 to 2 mm. The time beginning with the placement of the drop until the complete penetration of the sealing liquid into the paper (detectable by the vanishing gloss) was measured. For the purpose of better detection, 0.04% dye (acid rhodamine, Duasyn) by weight was added to the tested sealing liquids.

EXAMPLE 3

Implementation and Results of the Measurements for Sealing Liquids According to the Invention and Comparison Sealing Liquids The following letter envelopes which comprise distinctly different paper materials was tested. Designated as letter envelope 1 is OEKO-PIROL 90 White, window (229×324) mm, Order No. 71126/06/C4 2279 "OF Kuvermatic", Otto Ficker AG, Germany. Designated as letter envelope 22 is "Bless of Recycling", window (235×125) mm, Order No. 7140383-3602203, environmental label 14/9823, 100% recovered paper. Designated as letter envelope 108 is "POSTHORN" white, window C6/5 (229×114) mm, Order No. 2526149, Bong (previously Schmidt Papier), Germany. Designated as letter envelope 208 is "awamatic" high speed white, without window (229×324) mm, Art. No. 049080, automat envelopes by August Wegener GmbH & Co, Germany.

As commercially available sealing liquid, the following products were used or comparison purposes: sealing liquid "FT" of the company FrancoTech GmbH, Germany, "E-Z Seal" of the company Pitney Bowes, USA and "Quick Seal" preparation of the company Service Industries, USA, in the form as sold in Canada.

Tested as penetration agents were: EGDA (ethylene glycol diactet), DEGMEE (diethylene glycol monoethylether), EL (ethyl lactate) and EGMBE (ethylene glycol monobutylether). All these substances are obtainable from the company Merck, Germany.

SW designates a sealing liquid according to the invention.

Used as auxiliary agents were: NaLac (sodium lactate solution 50%, Merck, Germany), TMN 6 (Tergitol TMN 6 nonionic surfactant, Fluka, Germany), AM R 40 (ricinoleic amide propyl betaine, amphoteric surfactant sample, Degussa, Germany) and acid rhodamine BC 01 as a dye (Duasyn Merck).

Some measurement values regarding the surface tension (measured with KRÜSS K10ST ring tensometer) as well as the absorption time (which were obtained on letter envelope 108) are shown in the table I. One recognizes that no correlation exists between surface tension and absorption time. This proves that wetting agents per se are not also suitable as penetration agents and that penetration agents are important as components. Furthermore, one recognizes that the commercially available products FT and Quick Seal have absorption times such as water exhibits while sealing liquids according to the invention (DGMEE to SW) in contrast exhibit strongly reduced absorption times.

Absorption times for various letter envelopes are shown in the table II. One recognizes that strongly reduced absorption times compared to the commercially available sealing liquids are consistently obtained with sealing liquids according to the invention, and in fact on all tested letter envelopes (n.d.=not determined, 301=termination of the measurement after 5 min).

Finally, the wetting of the gum was tested, whereby for all sealing liquids with TMN 6 or AM R 40 good to very good wetting was consistently determined.

Overall, very short absorption times are achieved given combination of the penetration agent with a wetting agent.

Sealing times of a sealing liquid according to the invention in comparison with water are shown in the table III. The sealing liquid according to the invention is 2% EL, 0.5% AM R 40 and 1.2% NaLac. Infinite designates a sealing not achieved within the measurement time. Measurements were made at 25° C. and 21% relative humidity.

TABLE I

| Sample | Surface tension [mN/m] | Absorption time [s] |
| --- | --- | --- |
| VE-water | 71.5 | 301 |
| FT | 56.8 | 301 |
| Quick Seal | 47.5 | 301 |
| DEGMEE 20% | 48.3 | 33 |
| ELEMENT 6% | 49.1 | 19 |
| EGDA 15% | 39.5 | 2.1 |
| SW | 35.1 | 14 |
| AM R 40 0.5% | 35.1 | 45 |

TABLE II

| Sample | Absorption times(s) for various envelopes | | | |
| --- | --- | --- | --- | --- |
|  | 1 | 22 | 108 | 208 |
| VE-water | 301 | 301 | 301 | 301 |
| FT | 301 | 301 | 301 | n.d. |
| Quick Seal | 301 | 301 | 301 | n.d. |
| E-Z Seal | 301 | 301 | 301 | n.d. |
| EGDA 5% | 97 | 184 | 35 | n.d. |
| EGDA 7% | 12 | 41 | 4.8 | n.d. |
| EGDA 10% | 2 | 17 | 4 | n.d. |
| EGDA 13% | 1.5 | 3.7 | 2 | n.d. |
| EGDA 15% | 1 | 4.7 | 2.1 | n.d. |
| DEGMEE 5% | 301 | 301 | 301 | n.d. |
| DEGMEE 10% | 165 | 139 | 89 | n.d. |
| DEGMEE 15% | 113 | 135 | 82 | n.d. |
| DEGMEE 20% | 30 | 46 | 33 | n.d. |
| EL 3%, NaLac 1.2% | 211 | 255 | 55 | n.d. |
| EL 6%, NaLac 1.2% | 108 | 134 | 19 | n.d. |
| EL 9%, NaLac 1.2% | 20 | 25 | 8 | n.d. |
| EL 12%, NaLac 1.2% | 5 | 19 | 5 | n.d. |
| EL 3.3%/NaLac 1.2%/ TMN 6 0.5% | 0.7 | 1.1 | 0.9 | n.d. |
| EL 2.0%/NaLac 1.2%/ AM R 40 0.5% | 35 | 24 | 14 | 34 |
| EL 2.0%/AM R 40 0.5% | 35 | 31 | 24 | 47 |

TABLE III

| Envelope | Water | Sealing liquid |
|---|---|---|
| 1 | infinite | 10 s |
| 22 | 10 s | 5 s |
| 108 | 10 s | 10 s |
| 208 | 8 s | 5 s |

We claim as our invention:

1. A method for sealing an enclosure for placement in a delivery stream for transporting the enclosure, said enclosure comprising an enclosure body having an access opening therein for insertion of an item into the enclosure, and a closure element having dried gumming thereon, said method comprising the steps of:
    wetting the dried gumming on the closure element with a sealing liquid comprising 2% ethyl lactate by weight, 0.5% rincinoleic amide propyl betaine amphoteric surfactant by weight, and 1.2% sodium lactate 50% solution, to produce a wetted closure element; and
    positioning the wetted closure element over the access opening in said enclosure body and pressing the wetted closure element against said enclosure body to seal said access opening.

2. A method as claimed in claim 1, wherein said enclosure is an envelope comprising an envelope body as said enclosure body and an envelope flap, connected to said envelope body, as said closure element, and wherein the step of positioning the wetted closure element over the access opening comprises folding the envelope flap over said envelope body and pressing the envelope flap against said envelope body.

3. A method as claimed in claim 2 comprising folding the envelope flap over the envelope body and pressing the envelope flap against the envelope body automatically in an envelope closing device.

4. A method as claimed in claim 1 wherein said enclosure body is a carton comprising carton flaps that fold to cover said access opening, and wherein said closure element comprises gummed tape, and wherein the step of positioning the wetted closure element over the access opening comprises placing the gummed tape over the carton flaps that are positioned to cover said access opening, and pressing the gummed tape against said carton flaps.

5. A method as claimed in claim 1 wherein said sealing liquid additionally comprises at least one substance selected from the group consisting of stabilizers, buffers, dyes, and aromatic substances.

6. A method as claimed in claim 1 wherein said sealing liquid additionally comprises:
    50 to 96.3% water by weight,
    0 to 10.0% stabilizers and/or buffers by weight,
    0 to 5.0% dyes by weight,
    0 to 5.0% aromatic substances by weight and
    wherein said ethyl lactate, said rincinoleic amide propyl bentaine amphoteric surfactant, said 50% sodium lactate solution, said water, said stabilizers and/or buffers, said dyes, and said aromatic substances always add to 100% by weight.

7. A method as claimed in claim 1 wherein said sealing liquid additionally comprises:
    70 to 96.3% water by weight,
    0 to 3.0% stabilizers and/or buffers by weight,
    0 to 2.0% dyes by weight,
    0 to 1.0% aromatic substances by weight,
    wherein said ethyl lactate, said rincinoleic amide propyl bentaine amphoteric surfactant, said 50% sodium lactate solution, said water, said stabilizers and/or buffers, said dyes, and said aromatic substances always add to 100% by weight.

8. A method as claimed in claim 1 wherein said sealing liquid additionally comprises
    80 to 96.27% water by weight,
    0.01 to 2.0% stabilizers and/or buffers by weight,
    0.01 to 1.0% dyes by weight,
    0.01 to 0.1% aromatic substances by weight,
    wherein said ethyl lactate, said rincinoleic amide propyl bentaine amphoteric surfactant, said 50% sodium lactate solution, said water, said stabilizers and/or buffers, said dyes, and said aromatic substances always add to 100% by weight.

* * * * *